(12) United States Patent
Zinn et al.

(10) Patent No.: US 6,428,703 B1
(45) Date of Patent: Aug. 6, 2002

(54) METHOD FOR PURIFYING BIOLOGICAL MARCROMOLECULES, AND CHROMATOGRAPHIC COLUMN FOR PERFORMING SAID METHOD

(75) Inventors: Thomas Zinn, Duren; Manfred Sieber, Nideggen; Robert Zeidler, Kreuzau, all of (DE)

(73) Assignee: Macherey Nagel GmbH & Co. (DE)

( * ) Notice: Subject to any disclaimer, the term of this patent is extended or adjusted under 35 U.S.C. 154(b) by 0 days.

(21) Appl. No.: 09/471,152

(22) Filed: Dec. 23, 1999

(30) Foreign Application Priority Data

Dec. 23, 1998 (DE) .......................... 198 59 703

(51) Int. Cl.[7] .............................. B01D 15/08
(52) U.S. Cl. ................ 210/635; 210/656; 210/659; 436/161; 536/254
(58) Field of Search ................ 210/635, 656, 210/659, 198.2; 436/161; 536/25.4

(56) References Cited

U.S. PATENT DOCUMENTS

| | | | | |
|---|---|---|---|---|
| 4,808,314 A | * | 2/1989 | Karplus | 210/638 |
| 5,030,352 A | * | 7/1991 | Varady | 210/502.1 |
| 5,045,190 A | * | 9/1991 | Carbonell | 210/656 |
| 5,389,449 A | * | 2/1995 | Afeyan | 428/523 |
| 5,747,663 A | * | 5/1998 | Colpan | 536/25.4 |
| 5,834,596 A | * | 11/1998 | Ageland | 530/412 |
| 5,981,736 A | * | 11/1999 | Coffman | 210/635 |
| 5,990,301 A | * | 11/1999 | Colpan | 536/25.4 |

FOREIGN PATENT DOCUMENTS

| | | | |
|---|---|---|---|
| EP | 0308239 | 3/1989 | 210/656 |
| WO | 9521177 | 8/1995 | 210/656 |
| WO | 9521179 | 8/1995 | 210/656 |
| WO | 9729113 | 8/1997 | 210/656 |

OTHER PUBLICATIONS

Marston Manthorpe, et al. "Gene Therapy by Intra–Muscular Injection . . . " Human Gene Therapy 4:419–131 (1993).
Yoshiotomi Aida et al., "Removal of endotoxin from Protein Solutions . . . " Journal of Immunological Methods 132 (1990) 191–195.

* cited by examiner

Primary Examiner—Ernest G. Therkorn
(74) Attorney, Agent, or Firm—Liniak, Berenato, Longacre & White, LLC

(57) ABSTRACT

The invention concerns a method for purifying biological macromolecules, e.g. nucleic acids or proteins, from starting materials, in which the macromolecules, contained in a biological solution, are purified on a chromatographic material, and in which endotoxins are partially or completely removed with the aid of a nonionic surfactant, which is characterized in that the surfactant and the biological solution are brought into contact immediately before or during the purification of the macromolecules on the chromatographic material.

12 Claims, No Drawings

METHOD FOR PURIFYING BIOLOGICAL MARCROMOLECULES, AND CHROMATOGRAPHIC COLUMN FOR PERFORMING SAID METHOD

The invention concerns a method for purifying biological macromolecules, e.g. nucleic acids or proteins, from starting materials, in which the macromolecules, contained in a biological solution, are purified on a chromatographic material, and in which endotoxins are partially or completely removed with the aid of a nonionic surfactant. The invention is furthermore based on a chromatographic column for performing this method which contains a chromatographic material enclosed by closure filters.

Gene therapy is increasingly being used for the treatment of certain diseases. For this purpose, preparations which contain macromolecules such as nucleic acids or proteins as their active ingredients are obtained from biological starting material, e.g. from bacteria modified by genetic engineering. The preparations are then introduced into the human body.

It is essential for the success of gene therapy that the preparation be free of toxic substances. Since the preparations in question are usually isolated from bacteria such as the Gram-negative enterobacterium *E. coli*, and these bacteria contain as cell-wall constituents lipopolysaccharides (LPSs) that are also referred to as endotoxins, the removal of such endotoxins is very important. The reason is that intravenously administered preparations can cause fever, inflammatory reactions, or irreversible shock if they contain even small concentrations of endotoxins.

Various methods are known for removing the endotoxins. In a number of methods, this is done by using nonionic surfactants, for example the Triton X-114® surfactant of the Rohm & Haas company, specifically in conjunction with the method utilized for purifying and isolating the macromolecules. With these methods, the biological starting material containing the macromolecules is digested using a common method. Cell digestion can be accomplished by so-called alkaline lysis, by the action of high temperatures (boiling lysis), by the action of mechanical forces (compression/expansion, French press), or by the action of enzymes or detergents that destroy the cell membrane. Cell debris is then removed from the resulting cell lysate by mechanical methods, for example filtration or centrifuging.

In a subsequent step, the resulting lysate (also called "cleared lysate") is purified chromatographically. This is done by binding the macromolecules contained in the lysate to a chromatographic material having an anion exchange function. What is used in the existing art is a cartridge into which the chromatographic material is inserted. This can preferably be a porous or nonporous, inorganic or organic sorbent modified with an anion exchange function. A washing buffer is added in order to remove undesired substances. This is followed by elution of the macromolecules by adding an elution buffer. The eluted macromolecules are precipitated and are then available for further applications.

To remove the endotoxins, Aida et al. (Journal of Immunological Methods, 132 (1990), 191–195) and Manthorpe et al. (Human Gene Therapy 4 (1993), 419–431) recommend adding Triton X-114® surfactant to the solution with the macromolecules (once they have been chromatographically isolated and purified), and incubating the solution. The endotoxins bound to the surfactant are then removed by phase separation via centrifuging. A phase separation of this kind can be achieved, however, only if temperature conditions are strictly observed, temperature control of the centrifuge that is used being particularly complex. Repeated incubation at temperatures of 50° C. or 40° C. can cause irreversible damage to sensitive molecules.

EP-A-0 308 239 proposes removing endotoxin from an aqueous, purified, biologically usable, macromolecule-containing solution by adding a dialysable surfactant to the solution, and then bringing the solution into contact with a water-insoluble endotoxin sorbent in order to bind the endotoxins to the sorbent. The remaining liquid phase is then separated from the sorbent, and the surfactant is removed by dialysis. This yields a surfactant-free aqueous solution of the biological macromolecule, with a reduced concentration of endotoxins, which is usable for in vivo applications.

A similar method is evident from WO 97/29113. With this method the endotoxins are removed, after purification of the nucleic acids, in a further step using hydroxylapatite chromatography. In both cases, there is an increased outlay in terms of equipment, and the time required is considerable.

WO 95/21177 and WO 95/21179 propose, in addition to other methods for endotoxin removal, adding to the filtered or centrifuged lysate (cleared lysate) a buffer that contains, inter alia, 10% Triton X-100® or Triton X-114®. The solution is preincubated for a long period at low temperatures before being passed on for chromatographic purification. This method has the same disadvantages as the method described above. In addition, with all the methods the removal of endotoxins requires an additional process step, which considerably lengthens and complicates the purification and isolation procedure. In the case of sensitive nucleic acid molecules, this can result in decreased yield.

It is the object of the invention to make available a method for producing biological macromolecules containing little or no endotoxin that can be performed easily, quickly, and thus economically, and is also reliably reproducible. A further object is to make available a chromatographic column for carrying out this method.

According to the present invention, this object is achieved in that the surfactant and the biological solution are brought into contact immediately before or during the purification of the macromolecules on the chromatographic material. The basic concept of the invention is thus to remove endotoxins from the macromolecule-containing biological solution by the fact that the endotoxins enter into interaction with surfactants simultaneously with and in the same place as the chromatographic purification of the biological macromolecule, and thus do not bind to the chromatographic material and consequently can be washed out of the chromatographic material; the washing-out operation can be assisted by the use of detergent-containing solutions. It has been found, surprisingly, that very effective depletion of endotoxins can hereby be achieved with no need for time-consuming incubation and extraction steps. Since endotoxin removal takes place simultaneously with the purification and isolation of the macromolecules on the chromatographic material, a definite economy in terms of time and effort is attained.

The term "surfactant" is also to be understood as a mixture of different surfactants. In this context, the surfactant should belong to the group of the polyethylene glycol ethers, and preferably should be Triton X-114®.

It has proven to be particularly advantageous to supply the nonionic surfactant as a constituent of washing buffers that are used in any case on the chromatographic material. Alternatively or (better yet) in combination therewith, the chromatographic material, and/or a closure filter in a chromatographic column containing said material, should be impregnated with the surfactant. The surfactant should be present in the washing buffer and/or in the chromatographic material and/or in the closure filter at a concentration of 0.1 to 10%.

With regard to the second portion of the object, provision is made according to the present invention for the closure filter and/or the chromatographic material itself to be equipped with a nonionic surfactant, for example Triton X-114®.

A porous or nonporous, inorganic or organic sorbent, modified with anion exchange functions, can be used as the chromatographic material. Suitable closure filters are macroporous, sintered glass or a similar plastic, as well as compressed or interwoven synthetic mats made of polyamide, polyester, polypropylene, cellulose, or combinations of said materials. Preferably the closure filter and/or the chromatographic material is impregnated with the surfactant. The surfactant should be present at a concentration of 0.1 to 10%. The closure filter can vary greatly in thickness. The greater the thickness, the more surfactant it can bind for the endotoxin removal process. Advantageously, the thickness is between 1 and 15 mm.

EXAMPLE
Purification of Plasmid DNA from *E. coli*

In an appropriate culture flask, an antibiotic (Ampicillin®, final concentration 100 µg/ml) was added to 100 ml LB medium, which was then inoculated with a single bacterial colony (*E. coli* strain DH5α, transformed with pBluescript® SK plasmid DNA) from a corresponding agar plate. The bacteria were incubated for 12–14 hours at 37° C. in an shaking incubator. The bacterial culture was then centrifuged down and the resulting pellet was resuspended in 12 ml resuspension buffer (50 mM Tris/HCl, pH 8.0, 10 mM EDTA, 100 µg RNAse A/ml); 12 ml lysis solution (200 mM NaOH, 1% SDS) was then added, mixed carefully by inversion, and incubated for 5 minutes at room temperature. 12 ml neutralization buffer (3.0 M potassium acetate, pH 5.5) was then added, and the solution was thoroughly mixed by inversion and incubated for 5 minutes on ice. The neutralized bacterial lysate was clarified by filtration through a pleated filter.

A Nucleobond® EF 500 cartridge containing a chromatographic material was equilibrated with 5 ml equilibration buffer (N2-EF, 100 mM TRIS/phosphate, pH 6.3, 15% ethanol, 900 mM KCl, 0.5% Triton X-114®). The bacterial lysate clarified by filtration was applied onto the cartridge. The following washing buffers were then delivered in succession to the cartridge: 4×12 ml buffer N3-EF (100 mM TRIS/phosphate, pH 6.3, 15% ethanol, 1150 mM KCl, 0.5% Triton X-114®, 4×12 ml N4-EF). Elution of the purified plasmid DNA was performed by adding elution buffer N5-EF (100 mM TRIS/phosphate, pH 7.0, 15% ethanol, 1500 mM KCl). The eluted DNA was precipitated by adding 0.7–0.8% isopropanol. After centrifuging (30 min >15,000 G), the DNA pellet was washed again with endotoxin-free 70% ethanol precooled to 4° C. After a drying step, the DNA was resuspended in endotoxin-free TE buffer.

What is claimed is:

1. A method for purifying biological macromolecules from starting materials, in which a biological solution containing macromolecules is purified by charging the biological solution on a chromatographic material, and in which endotoxins are partially or completely removed from the macromolecules by washing them out of the chromatographic material using a washing buffer and thereafter the macromolecules are eluted from the chromatographic material, wherein a nonionic surfactant and the biological solution are brought into contact immediately before or during the purification of the macromolecules on the chromatographic material, without a prior incubation period.

2. The method as defined in claim 1, wherein the surfactant is a polyethylene glycol ether.

3. The method as defined in claim 1, wherein the surfactant is present in the washing buffer.

4. The method as defined in claim 1, wherein:
   at least one of the chromatographic material and an inlet-side closure filter in a chromatographic column containing the chromatographic material is impregnated with the surfactant.

5. The method as defined in claim 1, wherein the surfactant is present in at least one of the washing buffer, the chromatographic material and an inlet-side closure filter in a chromatographic column containing the material at a concentration of 0.1 to 10%.

6. The method as defined in claim 1, wherein the chromatographic material retains the macromolecules during said removal of the endotoxins from the chromatographic material.

7. The method as defined in claim 1, wherein the chromatographic material is an anion exchange material.

8. The method as defined in claim 7, wherein the anionic exchange material is one of an organic material, an inorganic material, a porous material and a non-porous material.

9. The method as defined in claim 1, wherein:
   the macromolecules are eluted from the chromatographic material by application of an elution buffer to the chromatographic material.

10. A method for at least partially removing endotoxins from a biological solution of macromolecules, comprising the steps of:
    applying the biological solution to a chromatographic material;
    contacting the biological solution with a nonionic surfactant immediately before or during said application of the biological solution to the chromatographic material, without a prior incubation period;
    applying a washing buffer to the chromatographic material thereby washing the endotoxins from the chromatographic material, and thereafter eluting the macromolecules from the chromatographic material.

11. The method as defined in claim 10, wherein:
    the surfactant is present in at least one of the washing buffer and an inlet side filter of a chromatographic column containing the chromatographic material.

12. The method as defined in claim 10, including the further step of:
    mixing the biological solution with the nonionic surfactant immediately before application of the biological solution to the chromatographic material.

* * * * *